United States Patent
Miyagi et al.

(10) Patent No.: US 7,476,546 B2
(45) Date of Patent: Jan. 13, 2009

(54) METHOD FOR SINGLE OXYGEN ATOM INCORPORATION INTO DIGESTED PEPTIDES USING PEPTIDASES

(75) Inventors: Masaru Miyagi, Grand Forks, ND (US); K. C. Sekhar, Grand Forks, ND (US)

(73) Assignee: University of North Dakota, Grand Forks, ND (US)

(*) Notice: Subject to any disclaimer, the term of this patent is extended or adjusted under 35 U.S.C. 154(b) by 170 days.

(21) Appl. No.: 11/273,806

(22) Filed: Nov. 15, 2005

(65) Prior Publication Data

US 2006/0105415 A1 May 18, 2006

Related U.S. Application Data

(60) Provisional application No. 60/627,819, filed on Nov. 15, 2004.

(51) Int. Cl.
*G01N 1/00* (2006.01)
*C12P 21/06* (2006.01)

(52) U.S. Cl. .................. 436/174; 436/175; 435/68.1

(58) Field of Classification Search .................. None
See application file for complete search history.

(56) References Cited

U.S. PATENT DOCUMENTS

| | | | |
|---|---|---|---|
| 6,864,089 B2* | 3/2005 | Figeys et al. ............... 436/6 |
| 6,908,740 B2* | 6/2005 | Vandekerckhove et al. ... 435/7.1 |
| 7,166,441 B2* | 1/2007 | Nadler et al. .............. 435/23 |
| 7,195,751 B2* | 3/2007 | Pappin et al. ............. 424/1.81 |
| 7,244,411 B2* | 7/2007 | Nunez et al. .............. 424/1.69 |
| 2003/0138871 A1 | 7/2003 | Hellerstein |
| 2003/0175804 A1* | 9/2003 | James .................... 435/7.1 |
| 2003/0186326 A1* | 10/2003 | Regnier et al. ............ 435/7.1 |
| 2005/0032149 A1* | 2/2005 | Yao et al. ................ 435/23 |
| 2005/0186135 A1* | 8/2005 | Howes ................... 424/1.11 |
| 2006/0105416 A1* | 5/2006 | Pappin et al. ............ 435/23 |
| 2006/0263886 A1* | 11/2006 | Peters et al. ............. 436/56 |
| 2007/0015233 A1* | 1/2007 | Brancia ................. 435/23 |

FOREIGN PATENT DOCUMENTS

WO    WO 02/099435 A1 * 12/2002

OTHER PUBLICATIONS

Reynolds, K., et al., Jan. 2002, Journal of Proteome Research, vol. 1, No. 1, pp. 27-33.*
Yao, X., et al., Feb. 2003, Journal of Proteome Research, vol. 2, No. 2, pp. 147-152.*
Heller, M., et al., Jul. 2003, Journal of the American Society for Mass Spectrometry, vol. 14, No. 7, pp. 704-718.*
Antonov, V. K., et al., 1981, European Journal of Biochemistry, vol. 117, No. 1, pp. 195-200.*

* cited by examiner

*Primary Examiner*—Nashaat T. Nashed
*Assistant Examiner*—William W Moore
(74) *Attorney, Agent, or Firm*—Kinney & Lange PA

(57) ABSTRACT

Optimized enzymatic conditions incorporate a single oxygen atom into digested peptides using a peptidase. The incorporation of a single oxygen atom is especially useful for proteolytic $^{18}O$ labeling in comparative proteomics. The optimized proteolytic $^{18}O$ labeling minimizes the generation of a mixture of isotopic isoforms of the peptides resulting from incorporation of either one or two $^{18}O$ atoms. The outcome is accurate quantification of isotopically labeled peptides.

8 Claims, 1 Drawing Sheet

METHOD FOR SINGLE OXYGEN ATOM INCORPORATION INTO DIGESTED PEPTIDES USING PEPTIDASES

This application claims the benefit of U.S. Provisional Application No. 60/627,819 filed on Nov. 15, 2004, for "A Method for Single Oxygen Atom Incorporation into Digested Peptides Using Peptidases" by M. Miyagi and K. C. Sekhar Rao.

FIELD OF THE INVENTION

The present invention relates to a method for comparative proteomics using a peptidase under enzymatic conditions that incorporate a single oxygen atom into a digested peptide. The method employs a peptidase to incorporate a single $^{18}O$ atom into peptide set derived from a population of proteins at a conditioned state, which is compared to a second peptide set incorporated with a single $^{16}O$ atom derived from a population of proteins at a second conditioned state. Upon combining the two peptide sets, the populations of proteins are analyzed for qualitative and quantitative differences based on the content of $^{18}O$ atoms and $^{16}O$ atoms in digested peptides using mass spectrometry instrumentation. The method is advantageous to reduce errors due to random incorporation of a second oxygen atom introduced during digestion and after mixing the peptide sets.

BACKGROUND OF THE INVENTION

The completion of the genome sequencing of humans and other species and the emergence of new technologies in mass spectrometry have together fostered unprecedented opportunities for studying proteins on a large scale. It is expected that large scale quantitative measurements of protein expressions in different sets of samples, referred to as comparative proteomics, will advance our understanding of physiological processes and disease mechanisms. Comparative proteomic approaches have been applied to various biological samples to identify and quantify proteins that are up- or down-regulated in response to biological conditions. To date, there are two primary strategies used in current comparative proteomics; two dimensional gel electrophoresis (2D-PAGE) based strategy and mass spectrometry based in vitro stable isotope labeling strategy.

Although 2D-PAGE based methods have been a primary choice in comparative proteomics, 2D-gels are cumbersome to run, have a poor dynamic range, and are biased toward abundant and soluble proteins. In contrast, the mass spectrometry based stable isotope labeling strategy has a potential of overcoming most of the weaknesses of the 2D-PAGE based methods. If the stable isotope labeling can be achieved efficiently and equivalently for each distinct sample, then two samples are compared using isotopic ratios. Among the in vitro stable isotope labeling methods, proteolytic $^{18}O$ labeling is the simplest stable isotope labeling method and is expected to have the least methodological error (technical variations). Therefore, the proteolytic $^{18}O$ labeling method has a potential to be a central method in comparative proteomics.

Although promising, a major drawback of the proteolytic $^{18}O$ labeling method has been the generation of a mixture of isotopic isoforms upon proteolytic digestion resulting from the differential incorporation of either one or two $^{18}O$ atoms ($^{18}O_1/^{18}O_2$) into each digested peptide species generated. Typical serine proteases used include trypsin, Lys-C or Glu-C proteases. Unfortunately, past studies have found that the ratios of the first and the second $^{18}O$ atom incorporation vary significantly with peptide sequences, and thus, the ratios of $^{18}O_1$- and $^{18}O_2$-peptides cannot be predicted with any certainty. The quantifications of the peptides results in significant errors in calculating $^{16}O$- and $^{18}O$-labeled peptide ratios. In spite of more recent wide appreciation of this problem, no method has been reported to solve the problem.

A second significant drawback of using serine proteases that has been demonstrated for $^{18}O$ labeling is that digested peptide products continue to react with these proteases at the carboxyl termini. As a result, the serine proteases will catalyze oxygen back-exchange reaction when two digests, the first in $H_2^{16}O$ and the second in $H_2^{18}O$, are mixed together. A previous report demonstrated that trypsin catalyzed oxygen back-exchange reaction occurs and leads to inaccurate quantification.

SUMMARY OF THE INVENTION

Unexpectedly, the present invention has found that peptidases are able to preferentially incorporate only a single $^{18}O$ atom into each digested peptide under specific conditions. In addition, there is no evidence of significant enzyme catalyzed oxygen back-exchange reaction. Therefore, the invention has the unique property of resolving previous commercial problems in utilizing proteases in conjunction with $^{18}O$-labeled peptides to accurately quantify different protein populations. The invention eliminates prior drawbacks employing $^{18}O$ labeling with peptidases to provide for a highly accurate quantification method for comparative proteomics.

The present invention is a method for incorporation of a single oxygen atom into a digested peptide using a peptidase. A protein or set of proteins is treated with a peptidase under specific conditions that incorporate a single oxygen atom in the carboxyl terminus of the digested peptide. The present invention is further directed to the mass spectrometry comparison of protein expression in different biological conditions using a peptidase to incorporate a single $^{18}O$ oxygen atom into peptide set derived from a population of proteins at a conditioned state which is compared to a second peptide set incorporating $^{16}O$ oxygen atom derived from a population of proteins at a second conditioned state.

The first aspect of the invention is a method of incorporating a single oxygen atom into a digested peptide using a peptidase.

The second aspect of the invention is a method of incorporating a single oxygen atom into a digested peptide using a peptidase, a protein, and water. Preferably, the oxygen atom is an $^{18}O$ atom or $^{16}O$ atom and the water is $^{16}O$ water or $^{18}O$ enriched water.

The third aspect of the invention is a method of incorporating a single oxygen atom under optimized conditions into a digested peptide using a peptidase, a protein, and $^{18}O$ enriched water. Preferably, the oxygen atom is an $^{18}O$ atom or $^{16}O$ atom and the water is $^{16}O$ water and $^{18}O$ enriched water.

The fourth aspect of the invention is a method of incorporating a single oxygen atom into a digested peptide using a peptidase selected from a group consisting of exopeptidases (EC 3.4.11-19) or endopeptidases (EC 3.4.21-25 and 99).

The fifth aspect of the invention is a method of incorporating a single oxygen atom into a digested peptide using an exopeptidase selected from a group consisting of aminopeptidase (EC 3.4.11), dipeptidyl-peptidase (EC 3.4.14), tripeptidyl-peptidase (EC 3.4.14), carboxypeptidase (EC 3.4.16-18), peptidyl-dipeptidase (EC 3.4.15), dipeptidase (EC 3.4.13) or omega peptidase (EC 3.4.19).

The sixth aspect of the invention is a method of incorporating a single oxygen atom into a digested peptide using an endopeptidase selected from a group consisting of serine endopeptidases (EC 3.4.21), cysteine endopeptidases (EC 3.4.22), aspartic endopeptidases (EC 3.4.23), metalloendopeptidases (EC 3.4.24) and threonine endopeptidases (EC 3.4.25) and unassigned endopeptidases (EC 3.4.99).

In the seventh aspect of the invention, a metalloendopeptidase is peptidyl-Lys metallopeptidase (EC 3.4.24.20, Lys-N), peptidyl-Asp metallopeptidase (EC 3.4.24.33, endoproteinase Asp-N), thermolysin (EC 3.4.24.27) or mycolysin (EC 3.4.24.31).

The eighth aspect of the invention is a method for optimizing a buffer for the incorporation of a single oxygen atom into a digested peptide using a peptidase, a protein, and $^{18}O$ enriched water. Most preferably, the buffer is optimized for pH.

The ninth aspect of the invention is a method for the comparison of proteins under different biological conditions, wherein a digested peptide of one biological condition contains a single $^{18}O$ atom incorporated by a peptidase and a digested peptide of a second biological contains a single $^{16}O$ atom incorporated by the same peptidase. The digested peptidases are mixed and analyzed by mass spectrometry for the ratio of $^{18}O$ and $^{16}O$. The ratio of $^{18}O$ and $^{16}O$ is used to determine the increase or decrease in regulation of a specific peptide or protein in the two biological conditions.

The tenth aspect of the invention is a kit to incorporate a single oxygen atom into a digested peptide containing a peptidase and enriched $^{18}O$ water.

The eleventh aspect of the invention is a kit to incorporate a single oxygen atom into a digested peptide containing a peptidase, optimized buffer and enriched $^{18}O$ water.

"Biological condition" means any physiological or cellular condition of a plant, animal, microorganism, organ, cell or other biological material.

"Optimized buffer" means any buffer and its components that are optimized for the incorporation of a single oxygen atom into a digested peptidase using a peptidase. The buffer is optimized for conditions that include, but are not limited to, pH and salt concentration "Single oxygen atom" means at least a 90% incorporation as a single oxygen atom, and more preferably, 95%, 98% or greater of the incorporated oxygen atom is incorporated as a single oxygen atom into the digested peptide. Examples of oxygen atoms include, but are not limited to $^{16}O$ atoms and $^{18}O$ atoms.

"Stable oxygen isotope" means any stable isotope of oxygen such as $^{16}O$ and $^{18}O$.

"$^{18}O$ enriched water" means water containing at least 90% $^{18}O$ atom, and more preferably, 95%, 98% or greater, where $^{16}O$ oxygen atoms comprise the majority of the remainder of the oxygen atoms in water.

"$^{16}O$ water" means naturally occurring water.

DETAILED DESCRIPTION OF THE INVENTION

Figure 1:
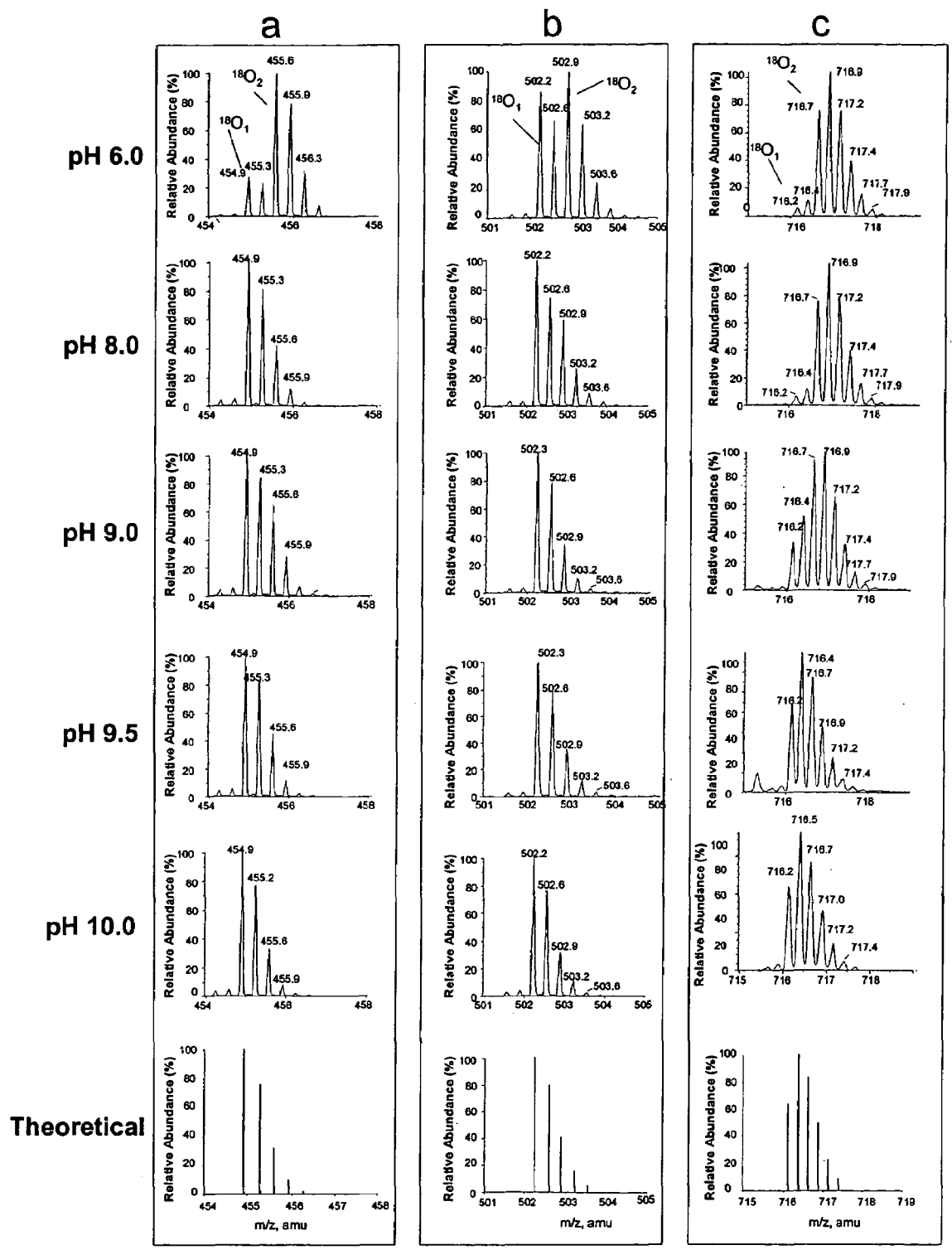
FIG. 1 shows the mass spectra of three peptides (a,b,c) obtained by digesting apomyoglobin with Lys-N in enriched $H_2^{18}O$ at different pH.

Traditionally mass spectrometry based comparative proteomic methods are based on in vitro labeling of two stable isotopes. For example, the peptides from the control sample are labeled with naturally abundant (light) isotope(s), while peptides from the experimental sample are labeled with its heavier isotope(s) or vice versa. The samples are then mixed together in equal proportion and analyzed by mass spectrometry. Since a peptide labeled with the light isotope and the same peptide labeled with the heavier isotope give different molecular weights, the light- and heavy-peptide can be distinguished by mass spectrometry. By comparing the peak areas or intensities of the light-peptide and heavy-peptide, the relative abundance of the two peptides can be determined. These ratios can further be used to quantify the relative abundance of each parent protein in the distinct original samples.

As a further illustration of the commercial application, using this comparative approach a pool of isotopically labeled proteins acquired from an unstressed system is mixed with the same relative amount of an unlabeled sample from a second (stressed) experimental system or vise visa. The combined pool is then analyzed by mass spectrometry to rapidly determine those stressed induced proteins relative to the unstressed state. The applications of this method would be highly useful to identify and quantify changes in protein expression in a variety of diseased or physiological states in animals, plants and microorganisms.

Currently, there are two ways to incorporate stable isotopes into peptides; first, by derivatization of peptides by a light- or heavy-isotope coded reagent (Isotope Coded Affinity Tag or ICAT) or second, by incorporation of $^{16}O$ and $^{18}O$ atom(s) into the carboxyl termini of peptides from the solvent water, $H_2^{16}O$ or $H_2^{18}O$, respectively, upon proteolytic cleavage of proteins. The second method is referred as proteolytic $^{18}O$ labeling, where a peptidase is used.

The members of the peptidase family are any enzymes that hydrolyze peptide bonds (EC 3.4, Enzyme Nomenclature 1992, Academic Press, San Diego, Calif.). Peptidases are present in the wide variety of biological sources and contain the amino acid sequence motif comprising His-Glu-Xaa-Xaa-His, where Xaa is any amino acid. The peptidase family can be subdivided into exopeptidases (EC 3.4.11-19) and endopeptidases (EC 3.4.21-99), the latter referred to as proteinases, that act near the terminus of the polypeptide or internally, respectively. Subclasses of exopeptidases include those acting at a free N-terminus releasing a single amino acid (aminopeptidase, EC 3.4.11), a dipeptide (dipeptidyl-peptidase, EC 3.4.14), or a tripeptide (tripeptidyl-peptidase, EC 3.4.14) and those acting at a free C-terminus releasing a single amino acid (carboxypeptidase, EC 3.4.16-18) or a dipeptide (peptidyl-dipeptidase, EC 3.4.15). Other exopeptidases are specific for dipeptides (dipeptidases, EC 3.4.13) or remove terminal residues that are substituted, cyclized or linked by isopeptide bonds (omega peptidases, EC 3.4.19). Subclasses of endopeptidases (EC 3.4.21-24 and EC 3.4.99) are subdivided on the basis of catalytic mechanism and specificity is used only to identify individual enzymes within the groups.

Subclasses of endopeptidases include serine endopeptidases (EC 3.4.21), cysteine endopeptidases (EC 3.4.22), aspartic endopeptidases (EC 3.4.23), metalloendopeptidases (EC 3.4.24) and threonine endopeptidases (EC 3.4.25). Endopeptidases that could not be assigned to any of the sub-subclasses EC 3.4.21-25 were listed in sub-subclass EC 3.4.99.

Unexpectedly, in the present invention members of the endopeptidase subfamily circumvented the incorporation of multiple $^{18}O$ atoms under specific enzymatic conditions. It is expected that conditions exist for other endopeptidases and exopeptidases that facilitate the incorporation of a single oxygen atom.

In the example described herein, peptidyl-Lys metallopeptidase (EC 3.4.24.20) is shown to incorporate a single oxygen atom into the carboxyl terminus of a digested peptide under alkaline pH conditions. Peptidyl-Lys metalloendopeptidase from *Grifola frondosa* (Lys-N, EC 3.4.24.20), which cleaves peptidyl-lysine bonds (-Xaa-Lys-) in proteins and peptides, is referred to as protease Lys-N because of its substrate specificity. The metalloendopeptidase contains one atom of zinc per molecule and is most active at pH 9.5. It is known to exhibit more than 50% maximal activity within the pH range of 6-10.5.

EXAMPLE 1

Sample Preparation Prior to $^{18}O$ Labeling of Proteolytic Peptides

The invention described herein employed a peptidase and $^{18}O$ enriched water to preferentially label the C-terminal fragment of the digested peptides; however this invention is not limited to and includes water containing any stable oxygen isotope. All reagents are available and the chemistry is generally well-known to those skilled in the art. The following examples are illustrations of such technology that may be used.

The first step may or may not include a protein denaturation step. In the event that information is required about the protein or peptide conformational state or structure this step would be omitted. For example, for a protein or peptide that plays a role in signal transduction and undergoes a conformational change or modification due to an altered physiological condition would be within the scope of this invention to assess changes through altered accessibility to proteases.

In cases where it is desirable to denature the protein or peptide to examine its primary structure or less structured state, the protein or peptide is treated to remove those elements required for secondary or tertiary structure. More specifically, the ability of any protease to fragment a protein or peptide is limited by the accessibility of the protease to susceptible peptide bonds. While denaturants such as acidic pH, urea, detergents, and organic co-solvents can partially denature proteins and expose many structurally shielded peptide bonds, pre-existing disulfide bonds within a protein can prevent sufficient denaturation with these agents alone. In conventional protein structural studies, disulfides are usually cleaved by reduction with 2-mercaptoethanol, dithiothreitol, and other reductants require a pH greater than pH 7 for sufficient activity. In the present experiments, reduction was achieved by using dithiothreitol and alkylation of cysteine thiol groups in proteins was established by using iodoacetoamide. To block thiol groups, a method used by Crestfield, et al. involved blocking the thiol (—SH) group by carbamidomethylation. The invention, however, is not limited to a specific method or agents to effectively denature part or all the protein or peptide structure. The examples described herein is presented as illustrative, where a protein or a mixture of proteins were reduced and subsequently carbamodomethylated before digestion with a metalloendopeptidase.

An illustrative example of the first step included the reduction and alkylation of cysteine thiol groups in a protein mixture consisting of bovine serum albumin (BSA), glycerol dehydrogenase (GDH), glyceraldehyde-3-phosphate dehydrogenase (GAPDH), ACY-I, creatine phosphokinase (CPK) and apomyoglobin. Approximately 2 nmoles of each of the protein were dissolved in 200 µl of 2 M Tris-HCl buffer (pH 8.0) containing 5 M guanidine-HCl and 2 mM ethylenediaminetetraacetic acid (EDTA) and subsequently reduced with 1 mM dithiothreitol (DTT) for 60 minutes at 50° C. followed by treatment with 2.5 mM iodoacetamide for 30 minutes at 25° C. The proteins of the reaction mixture were isolated from the reagents using a PD-10 gel filtration column (Amersham Biosciences AB, Uppsala, Sweden) that was equilibrated with 0.1% formic acid. The protein fractions from the PD-10 column were combined and dried in a Speed-Vac concentrator and dissolved in 100 mM glycine buffer (pH 10.0) containing 1M urea. The protein concentration was determined by a modified Bradford method. Because apomyoglobin does not contain cysteine or disulphide bonds, reduction and alkylation of apomyoglobin-only samples was not required.

EXAMPLE 2

Methods of Stable Oxygen Isotope Labeling and LC/MS Analysis

Denatured proteins, reduced and carbamidomethylated if necessary, were digested using either Lys-N or Asp-N metalloendopeptidase. The conditions for the proteolytic digestion were standardized in our laboratory for the purpose of single labeled oxygen atom incorporation. Lys-N was obtained from Seikagaku Corp. (Tokyo, Japan). The digestion of proteins by Lys-N was performed in the following buffer systems; 100 mM sodium phosphate at pH 6.0 or 8.0 or 100 mM glycine-NaOH at pH 9.0, 9.5, or 10.0. The digestion buffers were prepared from their corresponding stock solutions by placing the required aliquot into Eppendorf tubes, drying with a Speed-Vac concentrator and reconstituting with the appropriate stable oxygen isotope, preferably $H_2^{16}O$ or enriched $H_2^{18}O$. The digestions of proteins were incubated at 25° C. for 18 hrs using a Lys-N to substrate ratio of 1:85 (w/w), unless otherwise stated. The effective range of Lys-N to substrate (protein to be digested) ratios was found to be from 1:10 to 1:85.

After the incubation, the digests were diluted with 0.1% formic acid in $H_2^{16}O$ to the desired concentrations for mass spectrometry analyses. The resultant $^{18}O$ labeled peptides were analyzed by liquid chromatography mass spectrometry (LC-MS) that consisted of an UltiMate nano HPLC system (Dionex, San Francisco, Calif., USA) equipped with an isocratic pump, an autosampler, a gradient pump module and a column switching module and a QStar quadrupole/time-of-flight mass spectrometer (Applied Biosystem-MDS Sciex, Foster City, Calif., USA) equipped with nano-electrospray ion source (Applied Biosystem-MDS Sciex, Foster City, Calif., USA) and metal sprayer (GL Science, Tokyo, Japan). The protein digests (5 µl, ~1 pmol) were injected into a reverse-phase C18 trapping column (300 µm i.d.×1 mm, Dionex, Sunnyvale, Calif., USA) equilibrated with 0.1% formic acid/2% acetonitrile (v/v) and washed for 5 minutes with the equilibration solvent at a flow rate of 10 µL/min. After the washing, the trapping column was switched in-line with the reverse-phase analytical column and the trapped peptides were chromatographed on a column (0.075×50 mm, New Objective Inc., Woburn, Mass.) packed with Jupiter C18 media (10 μm, 300 Å, Phenomenex, Torrance, Calif., USA) using a linear gradient of acetonitrile from 2% to 82% in water in the presence of 0.1% formic acid over a period of 80 min at a flow rate of 200 nL/min. The column effluent was passed directly into the nano-electrospray ion source. The total ion current was obtained in the mass range of m/z 300-2000 at 2,100 V and 65 V of electrospray voltage and orifice voltage, respectively, in the positive ion mode. AnalystQS software (version 1.1.0.6410, Applied Biosystem-MDS Sciex, Calif., USA) was used for instrument control, data acquisition, and data processing. In liquid chromatography-tandem mass spectrometry (LC/MS/MS) analyses, the mass spectrometer was operated in data-dependent MS to MS/MS switching mode with the three most intense ions in each MS scan subjected to MS/MS analysis. The identities of the peptides were determined by submitting product ion spectra of the peptides to the Swiss Protein database using Mascot data base search software (Matrix Science, London, UK).

The actual $^{16}O/^{18}O$ peptide ratio for each peptide was calculated from the observed monoisotopic peak intensity of $^{16}O$- and $^{18}O$-labeled peptide present in mixed samples using the following equations.

Equations

1. $act^{16}O = obs^{16}O - (0.005 \times act^{18}O)$

2. $act^{18}O = obs^{18}O - (obs^{16}O \times Y) + (0.05 \times act^{18}O)$

3. $act^{16}O = obs^{16}O - 0.05 \times \frac{(obs^{18}O - obs^{16}O \times Y)}{0.95}$ 4. $act^{18}O = \frac{obs^{18}O - (obs^{16}O \times Y)}{0.95}$ 5. ratio of $^{16}O/^{18}O = act^{16}O/act^{18}O$ In these equations, $act^{16}O$ and $act^{18}O$ are the actual, corrected monoisotopic peak intensities (cps) arising solely from the peptides in sample 1 that were digested in 100% $H_2^{16}O$ and from the peptides in sample 2 that were digested in 95% $H_2^{18}O$ and 5% $H_2^{16}O$, respectively. The actual monoisotopic peak intensities are derived from the observed monoisotopic peak intensities (cps) of $^{16}O$- and $^{18}O$-labeled peptides, $obs^{16}O$ and $obs^{18}O$, arising from either sample. Y is the theoretical fractional intensity of the M+2 isotopic peak of the $^{16}O$-labeled peptide compared to its monoisotopic peak and is calculated from the amino acid sequence of the peptide. The M+2 isotopic peak is naturally occurring peptide in the $^{16}O$-labelled sample due to the presence of $^{13}C$, $^{2}H$, $^{15}N$, $^{17}O$ etc.

Equation 1 includes a correction factor to account for the 5% incorporation of $^{16}O$ into peptides digested in $H_2^{18}O$ for conversion to the observed $^{16}O$ signal. To obtain the signal due only to the peptide in the $^{16}O$ sample, the second term on the right side of equation 1, $0.05 \times act^{18}O$, is subtracted from the observed signal, $obs^{16}O$.

Equation 2, for calculating the actual intensity of the $^{18}O$ sample peptide, includes two correction factors. First, to obtain the signal due only to the peptide in the $^{18}O$ sample, the second term on the right side, $obs^{16}O \times Y$ is subtracted from the observed signal, $obs^{18}O$. Second, the third term in Equation 2, $0.05 \times act^{18}O$, is added as the 5% correction for the $^{16}O$-labelled peptides in the $^{18}O$ sample.

Equations 1 and 2 are converted further to become equations 3 and 4, respectively. The ratios of $^{16}O$- and $^{18}O$-labeled peptide were calculated by dividing the actual intensity of $^{16}O$ labeled peptide by the actual intensity of $^{18}O$ labeled peptide (Equation 5).

Mass spectra used for the $^{16}O/^{18}O$ peptide ratio calculations were extracted from the total ion current (TIC) only if the signal intensities of the peptides were lower than 500 cps. If the signal intensities exceeded 500 cps at the top of the TIC peak, regions of the lower slope of the TIC peaks were used to extract the mass spectra to avoid peak saturations. Approximately 1,000 cps was the maximum signal intensity within the linear dynamic range of the detector in the instrument used.

EXAMPLE 3

Optimizing Digestion Conditions for Single Oxygen Atom Incorporation

Apomyglobin was digested by Lys-N at pH 6.0, 8.0, 9.0, 9.5 or 10.0 using $H_2^{18}O$ prepared in 100 mM glycine-NaOH buffer. The resulting digests were analyzed by liquid chromatography-mass spectrometry (LC/MS). FIG. 1 shows the mass spectra of three representative apomyoglobin peptides that were hydrolyzed at different pH. In FIG. 1, panel a shows (M+3H)$^{3+}$ ions of peptide KALELFRNDIAA (SEQ ID NO 1), panel b shows (M+3H)$^{3+}$ ions of peptide KHPGDF-GADAQGAMT (SEQ ID NO 2), and panel c shows (M+4H)$^{4+}$ ions of peptide KVEADIAGHGQEVLIRLFTGHPETLE (SEQ ID NO 3). The bottom most spectrum in each panel is the theoretical abundances of the isotopes for each corresponding peptide containing one $^{18}O$ atom. These results show that variability of the $^{18}O_1$- and $^{18}O_2$-peptide ratios is pH dependent. At pH 6.0, peptide peaks with two $^{18}O$ atoms ($^{18}O_2$) were abundant in all the three peptides. As the pH is increased there is a steady decrease in the incorporation of the second $^{18}O$ atom. In fact, the incorporation of the second $^{18}O$ atom was not observed at pH 9.5 and 10.0 as evidenced by the exact match of the relative intensities of the isotopes of the observed peptide mass spectrum compared to their theoretical abundances. This invention demonstrates for the first time that there exist enzymatic conditions for endopeptidases where only a single $^{18}O$ atom is incorporated. Enzymatic conditions were determined for incorporation of a single oxygen isotope into digested peptides using another endopeptidase. Using the same optimization method, Asp-N, peptidyl-Asp metallopeptidase (EC 3.4.24.33), was found to incorporate a single $^{18}O$ atom in a peptide between pH 8.0 to pH 9.0.

In a separate experiment, it was confirmed that there is no detectable non-enzymatic incorporation of $^{18}O$ atom into angiotensin II (DRVYIHPF) incubated in 100 mM glycine-NaOH buffer (pH 10.0) or 0.1% formic acid at 25° C. for 24 hrs (data not shown), confirming that significant oxygen back-exchange reaction does not take place during the incubation period and LC/MS analysis.

It was further demonstrated that the single $^{18}O$ atom incorporation property of Lys-N is not affected by temperatures ranging from about 25° C. to about 50° C. and urea concentrations ranging from about 0.5 M to about 4 M. The effective range of the buffer concentration for single $^{18}O$ atom incorporation single ranged from about 10 mM to about 500 mM glycine-NaOH buffer. The activity of the enzyme was highest at about 25° C. and about 1 M urea under the conditions employed as judged by the observed ion intensities and selected for further use.

Finally, four representative apomyoglobin peptides were hydrolyzed in either $H_2^{16}O$ and in $H_2^{18}O$ in 100 mM glycine- NaOH buffer (pH 10.0) containing 1 M urea at 25° C. The proportional abundances of the isotopes between $^{16}$O- and $^{18}$O-labeled peptides were identical, indicating that only one $^{18}$O atom was incorporated into each peptide in the presence of urea.

For other examples described herein, the standard digestion protocol of proteins by Lys-N uses a 100 mM glycine-NaOH buffer, pH 10.0, containing 1 M urea at 25° C., which is incubated for 18 hrs.

EXAMPLE 4

Evaluation of Protein Mixtures by Single Oxygen Incorporation Using Metalloendoproteases The digestion was performed using the standardized digestion protocol described above on a protein mixture containing six reduced and S-carbamidomethylated proteins; bovine serum albumin (BSA), glutamate dehydrogenase (GDH), glyceraldehydes-3-phosphate dehydrogenase (GAPDH), aminoacylase-1 (ACY-1), creatine phosphokinase (CPK) and apomyoglobin. This protein mixture was digested in $H_2^{16}O$ and $H_2^{18}O$ separately and mixed in 1:1 ratio. Approximately 50 ng of this mixture was analyzed by LC/MS. A total of 50 Lys-N peptides from the six proteins were selected to calculate the ratios of $^{16}$O- and $^{18}$O-labeled peptides ($^{16}O/^{18}O$). The identities of the peptides, based on amino acid sequences, were determined by submitting product ion spectra of the peptides to Swiss Protein database using Mascot data base search software in a separate LC/MS/MS experiment.

The average experimental $^{16}O/^{18}O$ ratios for BSA, GDH, GAPDH, ACY-1, CPK and apomyoglobin peptides were 1.08±0.22 (n=23), 1.05±0.06 (n=6), 0.92±0.17 (n=7), 1.01±0.04 (n=3), 1.12±0.18 (n=4) and 1.04±0.21 (n=7), respectively. More careful analysis revealed that in all cases only a single oxygen atom was incorporated. Ratios of twelve peptides, however, deviated more than 0.25 from the predicted 1:1 ratios. Nine peptides of the 12 peptides contained either Glu-Lys or Pro-Lys bond cleavage, suggesting that the reaction rate of Lys-N to Glu-Lys and Pro-Lys bond is slower than other Xaa-Lys bonds. The average experimental $^{16}O/^{18}O$ ratios and standard deviations (SD) for BSA, GAPDH, CPK and apomyoglobin become 1.01±0.08 (n=15), 0.98±0.09 (n=6), 1.03±0.06 (n=3) and 1.06±0.10 (n=5) when the 12 peptides are removed, demonstrating an excellent accuracy and reproducibility of the method. The average and the standard deviation values were calculated using different peptides within a same protein.

EXAMPLE 5

Dynamic Range of Metallopeptidase $^{18}$O Labeling

To demonstrate the utility of endopeptidase $^{18}$O labeling for comparative proteomics, apomyoglobin (about 3.4 µg) was digested using either Lys-N in $H_2^{16}O$ or $H_2^{18}O$ under the standarized protocol and mixed in different ratios. Three representative peptides were analyzed by LC/MS, which was repeated 5-times to obtain average experimental $^{16}O/^{18}O$ peptide ratios. The obtained average experimental $^{16}O/^{18}O$ peptide ratios were plotted against their theoretical ratios with relative standard deviation (RSD) values to evaluate the linearity of the quantification of $^{16}O/^{18}O$ peptide ratios. The correlation coefficients ($r^2$) of the linear regression lines for the three peptides were 0.9960 for KALELFRNDIAA, 0.9977 for KHPGDFGADAQGAMT, 0.9995 for KHGTVV-LTALGGILK, respectively, indicating good linearity with respect to the $^{16}O/^{18}O$ peptide ratios over the range of 0.11 to 9.

EXAMPLE 6

Characterization of Proteome Changes in Cytokine/Lipopolysaccharide (LPS) Treated Versus Untreated Human Retinal Pigment Epithelium (ARPE-19) Cells Human retinal pigment epithelium (ARPE-19) cells were obtained from the American Tissue Culture Collection (Rockville, Md.). Cells were cultured to approximately 80% confluency in T-175 flasks at 37° C. under 95% air and 5% $CO_2$ in Dulbecco's Modified Eagle Medium: Nutrient Mixture F-12 (Ham) 1:1 (DMEM-F12) with 10% fetal calf serum, 2% L-glutamine and 0.5% antibiotic/antimycotic. The cells, before harvesting, were either: 1) treated in growth medium for 24 h with a combination of cytokines/LPS consisting of human tumor necrosis factor α (TNF-α, 3.25 ng/mL, Upstate, Lake Placid, N.Y.), human interferon-γ (IFN-γ, 50 ng /mL, Upstate, Lake Placid, N.Y.) and *Escherichia coli* lipopolysaccharide (LPS, 10 µg/mL, Sigma-Aldrich, St Louis, Mo.) or 2) untreated for controls, keeping them in medium for 24 h. After 24 h, the medium was removed from the flask and the cells were washed with phosphate buffered saline (PBS) twice and DMEM-F12 once, and harvested in DMEM-F12 by scraping the cells from the flask. The harvested cell suspension was centrifuged at 150 g for 10 min at 4° C., the supernatant removed and the cell pellet stored at −80° C. until use.

The stored cell pellets were resuspended in 2.5 mL of 2% sodium dodecyl sulfate (SDS) in 50 mM Tris-HCl, pH 7.5 buffer and sonicated for 60 seconds. The resulting homogenate was centrifuged at 8,000 g for 30 min at 4° C. and the supernatant recovered. The extracted proteins were reduced by adjusting the solution to 1 mM dithiothreitol (DTT) and reacting for 2 h at 50° C.

After S-alkylation treatment was performed, protein digestion of protein samples from treated and untreated cells were carried out separately in $H_2^{16}O$ and $H_2^{18}O$ under the conditions described above. The treated and untreated digests were mixed in a 1:1 ratio, separated by strong cation exchange chromatography into eight fractions, which were each analyzed by reverse phase liquid chromatography-tandem mass spectrometry. Identities of the resulting peptides were determined by database searching, and the peak intensities of each $^{16}$O- and $^{18}$O-labeled peptide was obtained and corrected as described above.

In this study, a very large population of proteins, 1046, were sequenced and quantified. Of these, 584 proteins were identified, and the relative abundance of 562 of these proteins was effective for complex and detailed comparative analysis between proteomes in cytokine/LPS treated versus untreated ARPE-19 cells. This is the most comprehensive finding of a retinal pigment epithelium cell proteome thus far and demonstrates the unique utility of the present invention. These results are detailed in Rao et al., MCP Papers in Press, Jul. 5, 2005, DOI 10.1074/mcp.M500150-MCP200, which is incorporated by reference.

The description of the specific embodiments of the invention is presented for the purposed of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications and publications referenced herein are hereby incorporated by reference.

Other embodiments are within the claims.

The invention claimed is:

1. A method for the comparison of a protein under different biological conditions using mass spectrometry comprising the steps of:
   a. digesting said protein of a first biological condition into peptides with either a peptidyl-Lys metalloendopeptidase or a peptidyl-Asp metalloendopeptidase in a buffer using $^{18}O$ enriched water to incorporate a single $^{18}O$ atom into at least 90% of the digested peptides;
   b. digesting said protein of a second biological condition into peptides with said peptidyl-Lys metalloendopeptidase or peptidyl-Asp metalloendopeptidase in the buffer using $^{16}O$ water to incorporate a single $^{16}O$ atom into the digested peptides;
   c. mixing digested peptides containing enriched $^{18}O$ of the first biological condition and digested peptides containing $^{16}O$ of the second biological condition;
   d. performing mass spectrometry analysis of the relative ratio of $^{18}O$ and $^{16}O$ in said mixed digested peptides; and
   e. determining a ratio of labeled peptides to unlabeled peptides, wherein the ratio determined indicates a change in an amount of said protein of a second biological condition relative to an amount of said protein of a first biological condition.

2. The method of claim 1, wherein said comparison is used for the identification of a biological condition in an animal.

3. The method of claim 1, wherein said $^{18}O$ enriched water is 95% $H_2^{18}O$ and 5% $H_2^{16}O$.

4. The method of claim 1, wherein the protein digest of step (a) and the protein digest of step (b) further comprise digesting said protein with another peptidase which is an exopeptidase (EC 3.4.11-19) or an endopeptidase (EC 3.4.21-25 and 99).

5. The method of claim 4, wherein said exopeptidase is an aminopeptidase (EC 3.4.11), a dipeptidyl-peptidase EC 3.4.14), tripeptidyl-peptidase (EC 3.4.14), a carboxypeptidase (EC 3.4.16-18), a peptidyl-dipeptidase (EC 3.4.15), a dipeptidase (EC 3.4.13) or an omega peptidase (EC 3.4.19).

6. The method of claim 4, wherein said endopeptidase is a serine endopeptidase (EC 3.4.21), a cysteine endopeptidase (EC 3.4.22), an aspartic endopeptidase (EC 3.4.23), a metalloendopeptidase (EC 3.4.24) a threonine endopeptidase (EC 3.4.25) or an unassigned endopeptidase (EC 3.4.99).

7. The method of claim 6, wherein said metalloendopeptidase is thermolysin (EC 3.4.24.27) of mycolysin (EC 3.4.24.31).

8. The method of claim 1, wherein digesting said protein of the first biological condition comprises:
   denaturing said protein;
   blocking a thiol group; and
   digesting said protein with a peptidase in said buffer using $^{18}O$ enriched water.

* * * * *

UNITED STATES PATENT AND TRADEMARK OFFICE
CERTIFICATE OF CORRECTION

PATENT NO. : 7,476,546 B2
APPLICATION NO. : 11/273806
DATED : January 13, 2009
INVENTOR(S) : Miyagi Page 1 of 1

It is certified that error appears in the above-identified patent and that said Letters Patent is hereby corrected as shown below:

In the Specification

Col. 1, Line 10-13 should read

STATEMENT OF GOVERNMENT INTEREST
This invention was made with government support under Grant Nos. R03 EY014020, P20 RR016741 and P20 RR017699 awarded by the United States Department of Health and Human Services. The government has certain rights in the invention.

Signed and Sealed this
Nineteenth Day of November, 2013

Teresa Stanek Rea
*Deputy Director of the United States Patent and Trademark Office*

SEQUENCE LISTING

```
<160> NUMBER OF SEQ ID NOS: 3

<210> SEQ ID NO 1
<211> LENGTH: 12
<212> TYPE: PRT
<213> ORGANISM: human

<400> SEQUENCE: 1

Lys Ala Leu Glu Leu Phe Arg Asn Asp Ile Ala Ala
1               5                   10

<210> SEQ ID NO 2
<211> LENGTH: 15
<212> TYPE: PRT
<213> ORGANISM: human

<400> SEQUENCE: 2

Lys His Pro Gly Asp Phe Gly Ala Asp Ala Gln Gly Ala Met Thr
1               5                   10                  15

<210> SEQ ID NO 3
<211> LENGTH: 26
<212> TYPE: PRT
<213> ORGANISM: human

<400> SEQUENCE: 3

Lys Val Glu Ala Asp Ile Ala Gly His Gly Gln Glu Val Leu Ile Arg
1               5                   10                  15

Leu Phe Thr Gly His Pro Glu Thr Leu Glu
                20                  25
```